United States Patent [19]
Singer et al.

[11] Patent Number: 6,057,328
[45] Date of Patent: May 2, 2000

[54] METHOD FOR TREATING HYPEROXIA

[75] Inventors: Jack W. Singer, Seattle, Wash.; Edward Abraham, Denver, Colo.

[73] Assignee: Cell Therapeutics, Inc., Seattle, Wash.

[21] Appl. No.: 09/001,373

[22] Filed: Dec. 31, 1997

[51] Int. Cl.[7] .................................................. A61K 31/52
[52] U.S. Cl. .......................................................... 514/263
[58] Field of Search .............................................. 514/263

[56] References Cited

U.S. PATENT DOCUMENTS 5,629,423  5/1997  Klein et al. ............................... 544/48

FOREIGN PATENT DOCUMENTS 9513075  5/1995  WIPO .

OTHER PUBLICATIONS

Baeuerle et al., *Ann. Rev. Immunol.,* vol. 12, pp. 141–176, "Function and Activation of NF–κB in the Immune System," 1994.

Bossi et al., *Intensive Care Med.,* vol. 21, pp. 241–246, "Retinopathy of Prematurity," 1995.

Jaeschke et al., *J. Leukocyte Biol.,* vol. 61(6), pp. 647–653, "Mechanism of Neutrophil–induced Parenchymal Cell Injury," 1997.

Jain et al., *Pediatric Pulmonol.,* vol. 20, pp. 160–166, "Glutathione Metabolism in Newborns: Evidence for Glutathione Deficiency in Plasma, Bronchoalveolar Lavage Fluid, and Lymphocytes in Prematures," 1995.

Jensen et al., *J. Appl. Physiol.,* vol. 72(5), pp. 1902–1907, "Role of Tumor Necrosis Factor in Oxygen Toxicity," 1992.

Lindsey et al., *J. Surg. Res.,* vol. 56, pp. 543–548, "Pentoxifylline Attenuates Oxygen–Induced Ling Injury," 1994.

Naureckas et al., *Eur. Respir.J.* vol. 7, pp. 1397–1402, "Pentoxifylline Does Not Protect Against Hyperoxic Lung Injury in Rats," 1994.

Sackner et al., *Ann. Intern. Med.,* vol. 82, pp. 40–43, "Pulmonary Effects Oxygen Breathing," 1975.

Stogner et al., *The Annals of Pharmacotherapy,* vol. 26, pp. 1554–1561, "Oxygen Toxicity," 1992.

Tsuno et al., *J. Appl. Physiol.,* vol. 69, pp. 956–961, "Acute Lung Injury from Mechanical Ventilation at Moderately High Airway Pressures," 1990.

*Primary Examiner*—Phyllis G. Spivack
*Attorney, Agent, or Firm*—Stephen Faciszewski

[57] ABSTRACT

Disclosed are methods for treating conditions resulting from hyperoxia or mechanical ventilation comprising the administration of a compound of the formula:

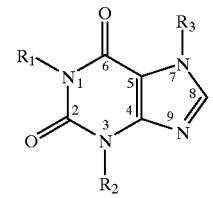

wherein $R_1$ is a substantially pure resolved R enantiomer ω-1, secondary alcohol-substituted ($C_{5-8}$) alkyl; and $R_2$ and $R_3$ are independently hydrogen atom or a ($C_{1-12}$) alkyl optionally containing one or two oxygen atoms in place of non-adjacent carbon atoms.

13 Claims, 1 Drawing Sheet time (hour)

METHOD FOR TREATING HYPEROXIA

TECHNICAL FIELD OF THE INVENTION

The present invention relates to treating conditions resulting from hyperoxia, and in particular, conditions resulting from therapeutic administration of oxygen. This invention also relates to conditions resulting from forced ventilation, including barotrauma resulting from mechanical ventilation. The methodology of the present invention comprises administration of a member of a class of enantiomerically pure xanthine compounds.

BACKGROUND OF THE INVENTION

Several medical conditions, for example, adult respiratory distress syndrome, laryngeal infections, interstitial lung disease, myocardial infarction, and general respiratory distress, require therapeutic administration of oxygen to compensate for deficient blood levels of oxygen. (See generally, Harrison's Principles of Internal Medicine, 13$^{th}$ ed., edited by Isselbacher et al., 1994). Such therapy can be as mild as constant release of oxygen via a tube placed just under or within the nostrils, or as drastic as mechanical forced ventilation for those who would otherwise be unable to breathe. In each case, practitioners have long been confronted with a well known side effect of this therapy: oxygen toxicity. Furthermore, in the case of mechanical ventilation, practitioners have also been concerned with barotrauma, or the physical disruption of cells and tissues due to unusually high air pressure within the lungs.

Practitioners of the art should suspect oxygen-induced lung injury in patients treated with high levels of oxygen (more than 50% oxygen, normal levels are about 21%) for extended periods of time, e.g., 5–7 days. Stogner et al., The Annals of Pharmacotherapy 26: 1554–1561, 1992. Animal and human studies indicate that the pathology of oxygen toxicity involves a latent period of 24–72 hours after hyperoxic exposure (100% oxygen), although evidence of injury has been seen in normal volunteers in as little as 3 hours. Sackner et al., Ann. Intern. Med. 82:40–43, 1975. The latent period is followed by an acute inflammatory phase marked by edema, alveolar hemorrhage, and inflammation, with variable degrees of necrosis of the pulmonary endothelium and type I pneumocytes. Stogner et al. The final phase involves hyperplasia of interstitial cells and type II pneumocytes, leading to hyaline membrane deposition, atelectasis, and pleural effusions. The end result of prolonged exposure to pure oxygen is death, which occurs in rats after 64 hours (on average) of exposure to 100% oxygen.

Oxygen toxicity is generally thought to be mediated by the action of reactive oxygen species ("ROS"). Such species include hydrogen peroxide, superoxide anion, singlet oxygen, and hydroxyl radical, which are produced in cell mitochondria as intermediates in the oxygen, and hydroxyl radical, which are produced in cell mitochondria as intermediates in the cytochrome oxidase system. (Stogner et al.). One to five percent of the oxygen entering this system is released as ROS. In some cells, especially inflammatory cells such as polymorphonuclear cells and macrophages, ROS are produced by additional cellular mechanisms, presumably as part of the body's anti-microbial defenses. Under normal oxygen conditions, cellular anti-oxidant defenses (such as described below) are sufficient to protect the cell from these reactive molecules. However, under hyperoxic conditions, the relative rise in ROS can overwhelm these defenses.

ROS are thought to cause damage by reacting with various molecules, including proteins, nucleic acids, and membrane lipids, thus destroying their functionality. Reactions with polyunsaturated fatty acids can lead to formation of lipid peroxides, which are powerful inhibitors of various enzymes and may undergo further reaction to form other reactive species. Certain ROS, especially hydroxyl radical, are particularly reactive, such that they nearly always react in the vicinity where they were formed. However, other species, such as hydrogen peroxide and super oxide anion, can diffuse away from the site of formation and cause further damage away from the site of formation.

A number of natural defenses against oxygen toxicity exist. These include catalase, which catalyzes the conversion of hydrogen peroxide to water and oxygen, superoxide dismutase (SOD), involved in the conversion of superoxide anion into hydrogen peroxide, and the glutathione redox cycle, which effects the reduction of both hydrogen peroxides and lipid peroxides. A number of other natural molecules, including vitamins A, C, and E, have anti-oxidant activity. Because one of the more important types of damage caused by ROS is peroxidation of polyunsaturated membrane lipids, lipid-soluble free radical scavengers such as vitamin E are thought to be particularly important in protecting against this kind of damage.

Inflammatory cells and cytokines play an important role in oxygen toxicity. For example, superoxide anion is a chemotactic agent for neutrophils and macrophages. These recruited cells can augment tissue destruction through release of inflammatory cytokines such as tumor necrosis factor (TNF) and interleukin-1 (IL-1) (which perpetuate the inflammatory response). Proteases such as elastase are also released, causing direct damage to tissues. Furthermore, neutrophils can release relatively large quantities of ROS through a mechanism called the respiratory burst, in which reactive oxygen species are generated within microsomes of the cell and released into the extracellular milieu.

The cytokine TNF plays a particularly significant role in oxygen toxicity. TNF has been shown to alter the mitochondrial respiratory chain so as to produce increased ROS. Baeuerle et al., Ann. Rev. Immunol. 12:141–179, 1994. This effect is toxic to cells lacking sufficient defenses against this rise in ROS, but the cytotoxic effect is suppressed in cells which overproduce manganese-dependent SOD (MnSOD). Interestingly, TNF itself induces the MnSOD gene. Thus, TNF potentially increases oxidative species while simultaneously increasing the cellular defense against such species.

Jensen et al. have shown that TNF directly mediates at least some of the toxicity of hyperoxia by showing that treatment with anti-TNF antibody improved the survival of mice exposed to high levels of oxygen. J. Appl. Physiol. 72(5):1902–1907, 1992. Furthermnore, pretreatment of the mice with sub-lethal doses of TNF prior to or soon after exposure to oxygen provided similar protection. This latter protection is thought to result from TNF's ability to induce MnSOD.

NF-κB is a factor closely associated with cellular responses to pathogenic conditions. Baeuerle et al. NF-κB up-regulates multiple inflammatory cytokines, such as TNF, and is activated by many of those same cytokines, including TNF. Baeuerle et al. Hydrogen peroxide was also found to activate NF-κB. As explained above, TNF induces MnSOD, which converts superoxide to hydrogen peroxide and would therefore provide a sufficient level of hydrogen peroxide to activate NF-κB, which in turn upregulates TNF. Thus, conceivably, hyperoxia could result in a self-perpetuating local inflammatory response.

The inflammatory component of oxygen toxicity is exacerbated by barotrauma caused by mechanical ventilation. Barotrauma has been described as cellular and ultrastructural pathologic changes in pulmonary parenchymal cells resulting from excessive intrapulmonary ventilatory gas pressure. Tsuno et al., J. Appl. Physiol. 69(3):956–961, 1990. Thus, mechanical ventilation has been shown to cause pneumothorax, pneumomediastinum, subcutaneous emphysema, and pulmonary cellular damage. Tsuno et al. Such trauma can induce an inflammatory response, including recruitment and activation of neutrophils. Jaeschke et al., J. lleukocyte Biol. 61(6):647–653 (1997). Thus, mechanical ventilation can cause damage via several pathways.

Oxygen toxicity may well occur at normal atmospheric levels. Such a situation arises in individuals lacking the normal levels of anti-oxidants (SOD, glutathione, etc.) found in normal adults. This situation arises most commonly in premature newborns. For example, Jain et al. have shown that premature newborns have decreased glutathione levels. Pediatric Pulmonol. 20:160–166, 1995. Thus, premature newborns can be especially susceptible to respiratory distress as well as a condition called retinopathy of prematurity (ROP). ROP is characterized by retinal neovascularization eventually including the vitreous, possibly leading to retinal detachment and finally to blindness. A current hypothesis regarding the pathogenesis of this condition suggests that a hyperoxic atmosphere relative to the intrauterine environment disturbs the replication of mesenchymal spindle cells in the vanguard zone of the growing retina, causing formation of extensive gap junctions in these cells which may lead to release of angiogenic factors with subsequent neovascularization. Bossi et al., Intensive Care Med. 21:241–246, 1995. Of course, premature newborns suffering respiratory distress are likely to be administered oxygen, thus amplifying the problems caused by oxygen toxicity.

Currently there is no drug available that is effective in treating conditions resulting from hyperoxia. Attempts to treat these conditions have focused mainly on administration of oxygen radical scavengers such as SOD and Vitamin E, with mixed results. Stogner et al. Furthermore, conflicting conclusions were drawn from two different studies which tested the ability of a TNF inhibitor, pentoxifylline, to treat hyperoxia. Naureckas et al., Eur. Respir. J. 7:1397–1402, "Pentoxifylline does not protect against hyperoxic lung injury in rats," 1994. Lindsey et al., Journal of Surgical Research 56:543–548, "Pentoxifylline Attenuates Oxygen-Induced Lung Injury," 1994. Thus, there is a need in the art for a drug which will provide treatment for conditions resulting from hyperoxia.

An object of this invention is therefore to provide a therapeutic, prophylactic treatment for protecting against development of conditions resulting from hyperoxia, particularly, those conditions resulting from mechanical ventilation. A further object of this invention is to provide a treatment for oxygen toxicity and other conditions resulting from hyperoxia.

SUMMARY OF THE INVENTION

The present invention provides methods for treating conditions, preferably prophylactically, which result from hyperoxia or from forced ventilation. The inventive methods comprise administering to an individual in need of such treatment a pharmaceutically effective amount of a compound of the formula

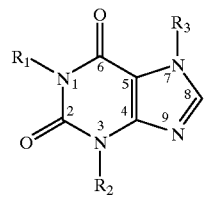

wherein $R_1$ is a substantially pure resolved R enantiomer $\omega$-1, secondary alcohol-substituted ($C_{5-8}$) alkyl; and $R_2$ and $R_3$ are independently a hydrogen atom or a ($C_{1-12}$) alkyl. Optionally, the ($C_{1-12}$) alkyl may contain one or two oxygen atoms in place of non-adjacent carbon atoms.

DETAILED DESCRIPTION OF PREFERRED EMBODIMENTS

Figure 1:
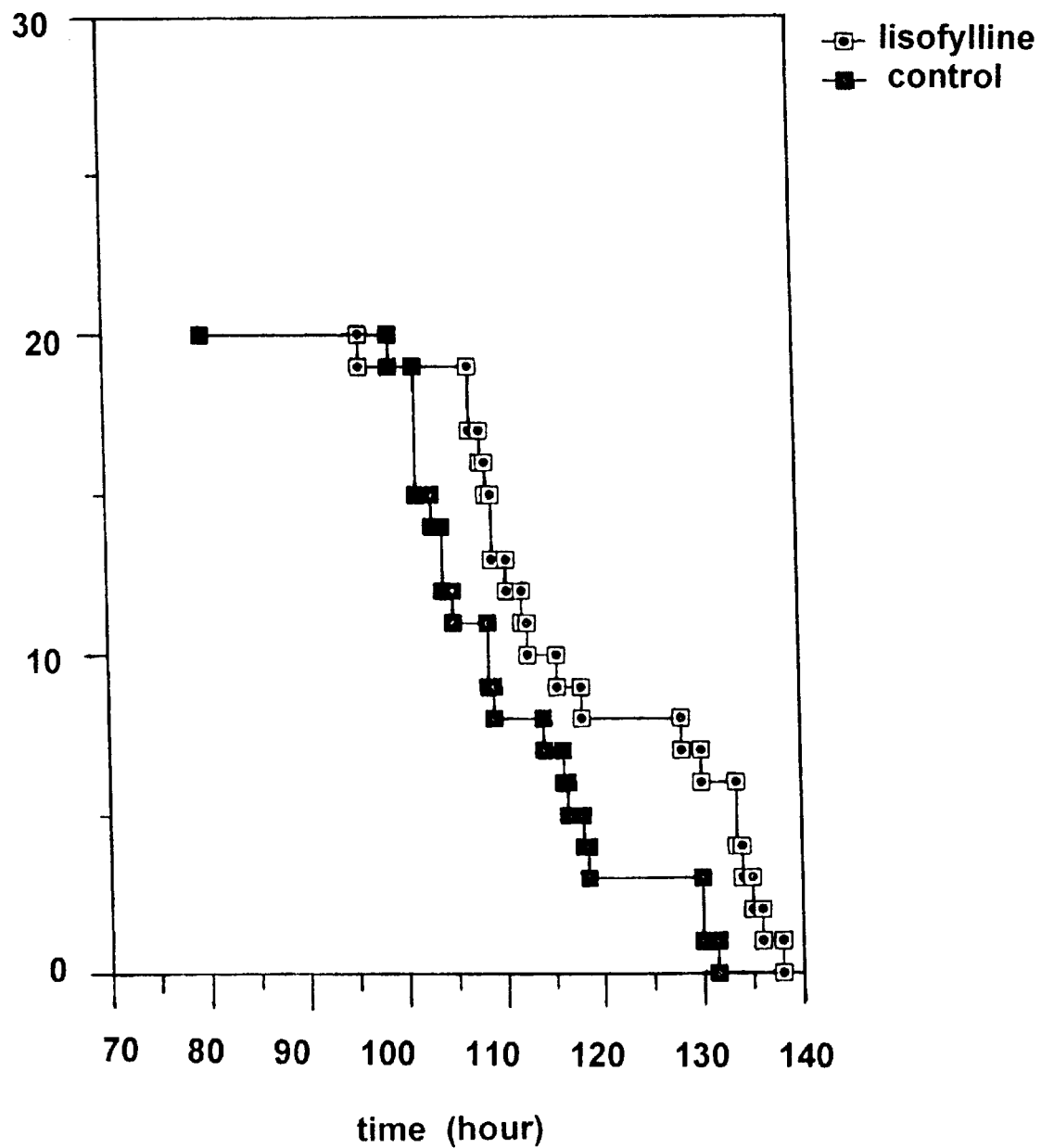
FIG. 1 shows data obtained in a hyperoxia survival study of mice exposed to 100% $FiO_2$ (Fraction of inspired $O_2$) which are either untreated or treated with 1-(R)-(S-hydroxyhexyl)-3,7-dimethylxanthine (LSF).

The inventive methods treat conditions resulting from hyperoxia. In the inventive methods, an individual in need of such treatment is administered a pharmaceutically effective amount of a compound formula

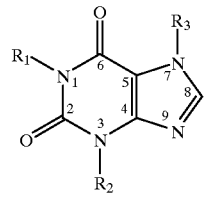

wherein $R_1$ is a substantially pure resolved R enantiomer $\omega$-1, secondary alcohol-substituted ($C_{5-8}$) alkyl; and $R_2$ and $R_3$ are independently hydrogen atom or a ($C_{1-12}$) alkyl. Optionally, the ($C_{1-12}$) alkyl may contain one or two oxygen atoms in place of non-adjacent carbon atoms.

The invention further provides methods for treating conditions resulting from forced ventilation comprising administering to an individual in need of such treatment a pharmaceutically effective amount of a compound of the above formula.

Preferably, the inventive method treats conditions resulting from mechanical or forced ventilation.

More preferably, the inventive method is useful in treating inflammation resulting from pulmonary cellular damage. In the most preferred embodiments of the inventive methods, the pharmaceutically effective amount is preferably a prophylactically-effective amount.

Preferably the inventive method comprises administering 1-(R)-(S-hydroxyhexyl)-3,7-dimethylxanthine.

In a preferred inventive method, the condition to be treated may result from elevated inspired oxygen levels. Other preferred methods may treat conditions which result from elevated barometric pressure. More preferably the inventive methods treat hyperoxia resulting from mechanical ventilation.

Alternatively, hyperoxia may result from normal oxygen levels at ambient barometric pressure.

Preferred conditions resulting from hyperoxia or mechanical ventilation and suitable for treatment are atelectasis, bronchopulmonary dysplasia, inflammation, tracheobronchitis, and retinopathy of prematurity.

Synthesis of Compounds Used in the Inventive Method

The following process for synthesizing compounds used in the inventive method is adapted from U.S. Pat. No. 5,629,423, the disclosure of which is incorporated in its entirety by reference herein.

In the first step, a hydroxyl group of an α-hydroxy ester starting material is activated with a leaving group to form an intermediate activated ester. Procedurally, the α-hydroxy ester is combined with a sulfonyl acid chloride in the presence of a base, with or without a solvent (if present, preferably an ester, ether, or hydrocarbon, more preferably toluene solvent) at temperatures ranging between 20–50° C. for 4–8 hours. Subsequent addition of mineral acid and washing the organic phase with a salt solution removes excess base. The product may be isolated by solvent removal as required. Preferred α-hydroxy ester starting materials include S-ethyl lactate and leaving groups include but are not limited to sulfonyl acid chlorides, notably, p-toluenesulfonyl chloride and methanesulfonyl chloride. Representative, preferred bases are pyridine and trialkylamines. Although a solvent is not required, solvents may be at least one of an ester, ether or hydrocarbon solvent. Preferred mineral acids and salt solutions include, for example, hydrochloric acid and sodium chloride or calcium chloride, respectively. In a preferred embodiment, the α-hydroxy ester is for example ethyl (S)-(–)-lactate, the leaving group is p-toluenesulfonyl chloride and a resulting ester product is ethyl (S)-2-p-toluenesulfonyloxy propionate. A schematic representation of this preferred reaction is shown below.

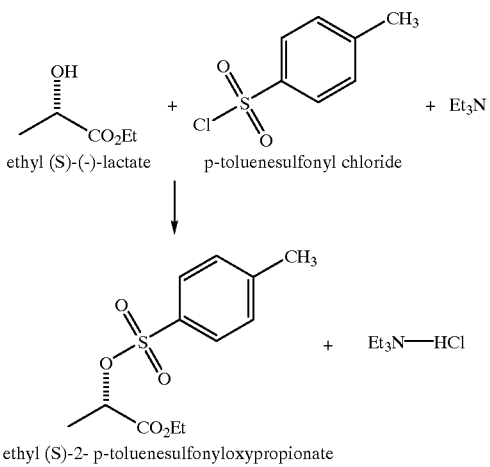

The intermediate activated ester is then converted to a first intermediate alcohol product by reacting the intermediate activated ester with a reducing agent in a solvent. Preferably, the activated ester and reducing agent are reacted at a temperature ranging from −40° C. to +80° C. Excess reducing agent is removed by addition of a suitable ketone reagent and addition of a solubilizing agent to hydrolyze any reducing agent-derived residue at a hydrolysis temperature ranging from 0° C. to +40° C. The resulting reaction mixture is filtered to remove precipitates and washed with aqueous solution. The solvent is finally removed to isolate the first intermediate primary alcohol. Preferred reducing agents are, for example, borane-tetrahydrofuran, borane-methylsulfide, diusobutyl aluminium hydride, sodium bis (2-methoxyethoxy) aluminium hydride, and sodium borohydride activated with methanol or acetic acid. Representative solubilizing agents include, but are not limited to, sodium carbonate, sodium hydroxide, hydrochloric acid, sulfuric acid and potassium sodium tartrate. Solvents may be at least one ether or hydrocarbon solvent, although other solvents are within the scope of the invention.

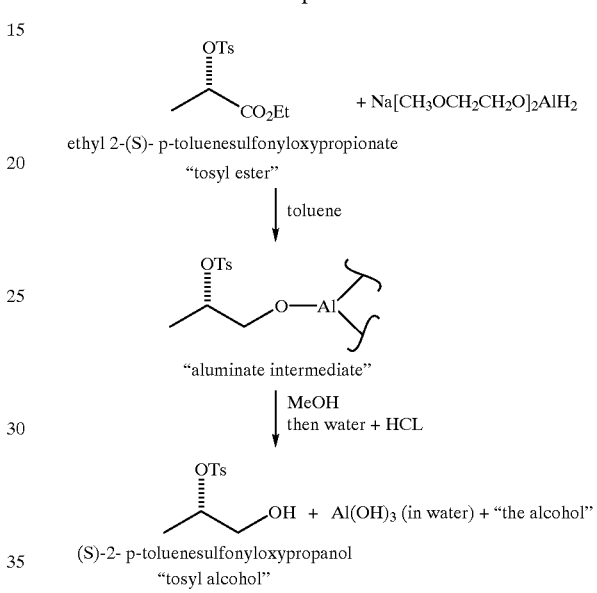

In a deprotonation reaction, the first intermediate alcohol product is reacted with a base to form an alkoxide, which reacts in an intramolecular substitution reaction with the leaving group to form a chiral oxirane. This substitution step also inverts the stereochemistry of the starting material.

Reacting the first intermediate alcohol product and a base in a solvent, while maintaining a solution temperature ranging from 0° C. to 90° C. yields the desired oxirane product, thereby inverting the stereochemistry of the starting material. The resulting oxirane is isolated by distillation from the heated reaction or by extraction into a solvent, with the to solvent/oxirane mixture being subsequently distilled. Representative bases include: sodium, potassium or calcium hydroxide, potassium tert-butoxide, potassium hydride and sodium or potassium carbonate. Solvents may be selected from aqueous, hydrocarbon, ether, polar aprotic and alcohol solvents. Preferred solvents include, but are not limited to: water and toluene. Schematically, a preferred process for preparing (R)-(+)-propylene oxide from a crude tosyl alcohol, inverting the chirality of the molecule, is shown below as (part a):

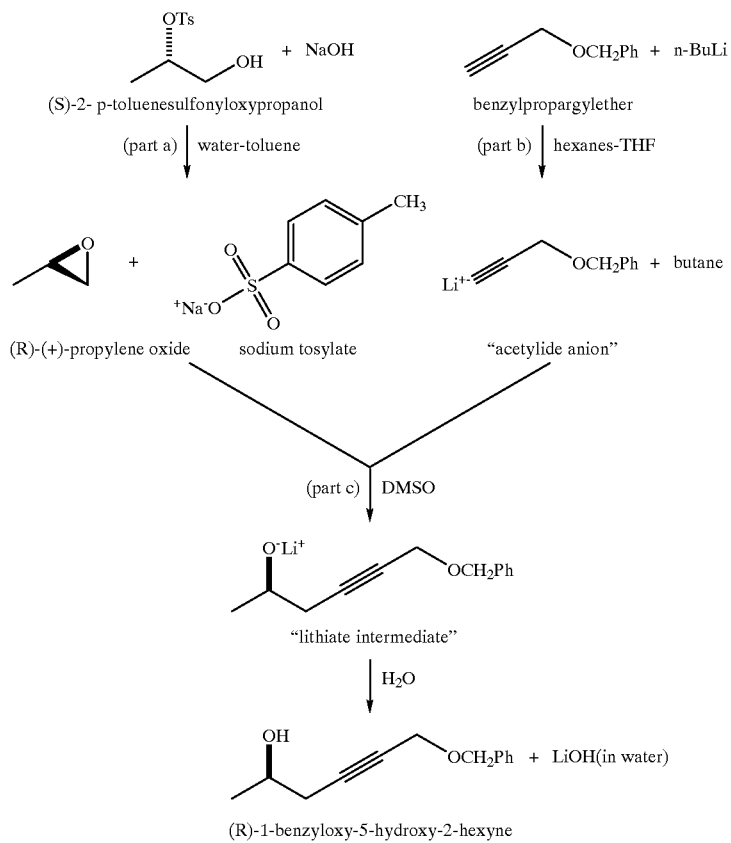

Or alternatively, a preferred part a of this step is schematically represented below:

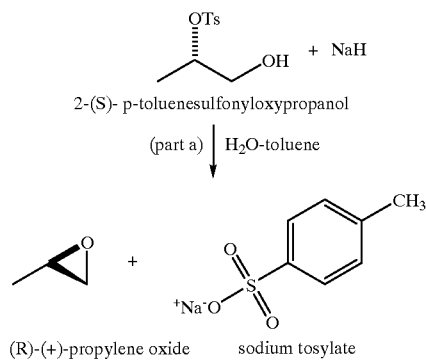

Preparation of a second reaction product in the inventive process involves providing a terminal, $C_{3-10}$ alkynyl primary alcohol. A first primary hydroxyl group of the alkynyl alcohol is converted to an alkali-stable group (preferably ether or acetal), forming an alkynyl intermediate. Most preferred alkynyl intermediates are ethers.

The alkynyl intermediate is prepared using a $C_3$ alkynyl primary alcohol and reacting this alcohol with an electrophile. Generally, in the inventive process, electrophiles include, but are not limited to, benzyl halides (preferably chloride, bromide or iodide) and are reacted with the alkoxide generated from the alkynyl alcohol with strong bases. Representative bases are potassium or sodium hydroxide, potassium carbonate and sodium hydride. Reaction times are decreased by the presence of tetraalkyl and arylalkyl ammonium salt phase transfer catalysts. Preferable catalysts may be tetrabutyl ammonium bromide, tetrabutyl ammonium hydrogen sulfate, tetrabutyl ammonium chloride, tributylmethyl ammonium chloride and tricaprylmethylammonium chloride. Catalysts such as alkali metal iodides, which generate benzyl iodide in situ, also facilitate ether formation. Suitable solvents are ethers or hydrocarbons (toluene, hexane, heptane) and aqueous bases where applicable. Suitable reaction temperatures vary between 10 and 90° C., and preferably, the alkynyl intermediate is isolated by extraction into an organic solvent with subsequent removal of the solvent by distillation. The most preferred reagents may be sodium hydroxide (base), tetrabutyl ammonium bromide. benzyl chloride (catalysts) and propargyl alcohol (primary alcohol).

In a preferred process, propargyl alcohol is reacted with benzyl chloride according to the following mechanism:

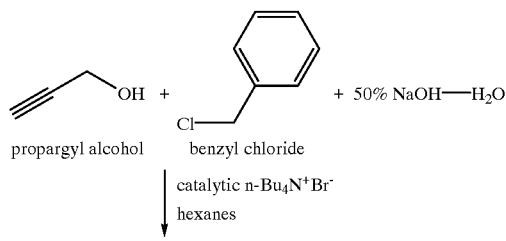

-continued

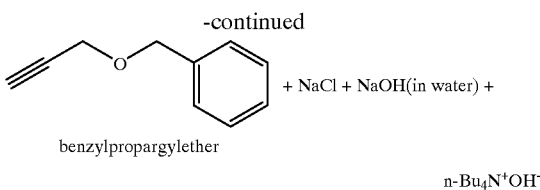

benzylpropargylether

+ NaCl + NaOH(in water) + n-Bu$_4$N$^+$OH$^-$

Next, the alkynyl intermediate is treated with a strong base, resulting in formation of an acetylide anion salt, having a mono- or di-valent cation. The alkynyl intermediate may be deprotonated with strong bases such as alkyl lithiums in hydrocarbon and ether solvents, metal amides in polar aprotic solvents and alkali metals in ammonia, naphthalene and styrene. Examples of solvents are heptane, tetrahydrofuran, dimethyl sulfoxide and N-methyl pyrrolidinone. Suitable reaction temperatures range from −20 to 70° C. The acetylide anion is used in solution for the next step. Preferred reagents are butyllithium (strong base) and heptane (solvent).

A preferred process for preparing a lithium anion salt of benzylpropargylether is schematically represented as part b, above.

The acetylide anion salt (the second reaction product) is then coupled to the chiral oxirane, prepared above. This step forms a second intermediate alcohol, having the alkynyl and alkali-stable groups. The acetylide anion is coupled to the chiral oxirane in a solvent. Preferred solvents include polar aprotic solvents or a Lewis acid in an ether solvent. Representative examples of preferred solvents are dimethyl sulfoxide, N-methyl pyrrolidinone, tetrahydrofuran and dioxane and Lewis acids may be, inter alia, boron trifluoride etherate and lithium perchlorate. Preferred reaction temperatures range from −20 to 65° C. The reaction product is isolated by extraction with ether or ester solvents and subsequently distilled.

Preferred reagents used in representative processes of the invention are chosen to give the optimum regioselectivity in the opening of the chiral epoxide, such as, for example, dimethylsulfoxide, N-methyl pyrrolidinone and lithium perchlorate in tetrahydrofuran/hexane give 0.15–0.35% of 5-hydroxy-1-benzyloxy-4-methyl-2-pentyne relative to 5-hydroxy-1-benzyloxy-2-hexyne. This equates to a regioselectivity of 99.65–99.85%. Schematically a preferred process for coupling the chiral oxirane to the acetylide anion is shown in part c, above.

In the next step, the alcohol group of the second intermediate alcohol is converted to an intermediate ester. The intermediate ester retains both the alkynyl and alkali-stable groups.

Generally, the alcohol group is converted to an ester by reaction with acid anhydrides or acid halides in the presence or absence of acids or bases. Representative acids or bases include, but are not limited to, acetic anhydride with phosphoric acid, perchloric acid, sulfuric acid or dimethyl aminopyridine. Preferably, acetyl chloride is used with triethylamine and dimethylaminopyridine. Reaction temperatures may range from 0 to 80° C. In this process step, excess reagent is removed by the addition of sodium carbonate or sodium bicarbonate. This reaction may be performed in the absence of solvents or in a solvent system, preferably, hydrocarbon solvents. The solvents may be heptane, toluene or ester solvents such as ethyl acetate. The product is isolated by distillation. Most preferred reagents may be sulfuric acid, acetic anhydride and sodium carbonate.

Subsequently, the unsaturated alkynyl group is hydrogenated, first to an alkenyl and then to an alkyl, saturated carbon-carbon bond. Prior to reducing the unsaturated bond, the substrate is treated with an aqueous solution of potassium peroxymonosulfate and decolorising charcoal to remove impurities. Alternatively, powdered nickel on a solid support (and similar systems) may also be used. Reduction is achieved using a transition metal catalyst. The transition metal catalysts may be, for example, nickel, palladium metal or hydroxide, platinum metal or oxide, rhodium, or ruthenium and hydrogen at elevated pressures. Corresponding hydrogen pressures generally range from 0 to 150 psi at temperatures ranging from 0 to 100° C. Alcohols, esters or hydrocarbons and the like are suitable solvents. The reaction can also be performed by transfer hydrogenation using cyclohexene and palladium. Most preferred reagents may be palladium on charcoal, heptane, and hydrogen.

Subsequently, the alkali-stable group is converted to a second primary hydroxyl group, leaving an alkyl intermediate ester having a second primary hydroxyl group. Preferably, this step is one of hydrogenolysis or mild acid hydrolysis of a corresponding alkali-stable ester, protecting the first primary hydroxyl group. This deprotection is achieved using transition metal catalysts such as nickel, palladium metal or hydroxide, platinum metal or oxide, rhodium, or ruthenium and hydrogen. Hydrogen pressures range from 0 to 150 psi at temperatures from 0 to 100° C. Alcohols, esters or hydrocarbons are suitable solvents. The reaction may also be performed by transferring hydrogenation using cyclohexene and palladium. Most preferred reaction reagents may be palladium on charcoal, heptane, and hydrogen.

A representative preferred reaction is illustrated in the schematic below:

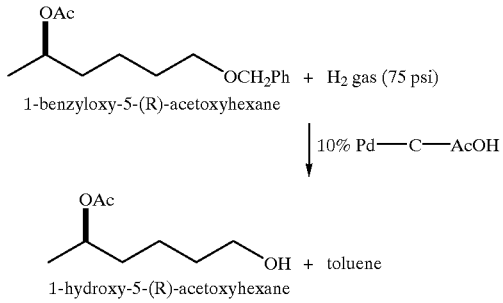

The second primary hydroxyl group is then replaced with a terminal leaving group, forming an ester precursor. The conversion of the alcohol to a halide may be accomplished by using acid halides and a base. Suitable acid halides include, but are not limited to, thionyl halides, phosphorus oxychloride, phosphorus trihalides, and oxalyl trihalides. Examples of bases are dimethyl formamide and pyridine. The reaction is performed in hydrocarbon solvents at suitable temperatures ranging from 0 to 70° C. Solvents may be selected from among, inter alia, heptane and toluene. The alcohol can be converted to an alkyl or aryl sulfonate leaving group as described above (see page 7 lines 10–25). The resulting alkyl or aryl sulfonate then may be converted to a halide leaving group by reaction with metal halides. Preferred leaving groups include, but are not limited to, halides (resulting in chiral, ester-halide precursor), aryl sulfonates or alkyl sulfonates (most preferably, halide). Representative metal halides include, for example, lithium chloride or bromide or sodium chloride or bromide. Suitable solvents for this transformation may be polar aprotic solvents such as dimethyl sulfoxide and acetone. Preferred reaction temperatures range from 20 to 110° C. A representative of a preferred embodiment of this synthetic step is show below:

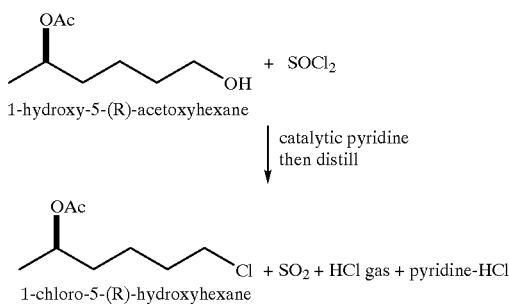

The terminal leaving group of the ester precursor is replaced with a core moiety substituent (either commercially available or prepared by another synthetic process). Generally, the ester precursor, having a leaving group, and selected nucleophile are reacted in a polar aprotic solvent at a temperature range of +40 to +100° C. Reaction times range from 6 to 24 hours. Representative polar aprotic solvents include, inter alia, dimethyl sulfoxide, acetonitrile, N,N-dimethylformamide. Next, the coupled ester precursor product is quenched with water, followed by extraction into an organic solvent. The organic phase is washed with a salt solution. The ester precursor is isolated by removal of the solvent via distillation. Suitable extraction solvents are esters, including ethyl acetate, propyl acetate, isopropyl acetate, butyl acetate and isobutyl acetate. Although other reagents are within the scope of the invention, preferred reagents include, for example, dimethyl sulfoxide (polar aprotic solvent), 1-chloro-5-(R)-acetoxyhexane (ester precusor), sodium theobromine (nucloephile) and isobutyl acetate (extraction solvent).

Via this process, the ester-protectcd chiral precursor can be coupled to a hetero atom in a heterocyclic moiety. One example, as shown schematically, couples the ester-protected chiral precursor to the N1 position of theobromine to form a chiral ester of a secondary alcohol with a 3,7-dimethylxanthine moiety.

A schematic representation of this preferred synthesis is shown below.

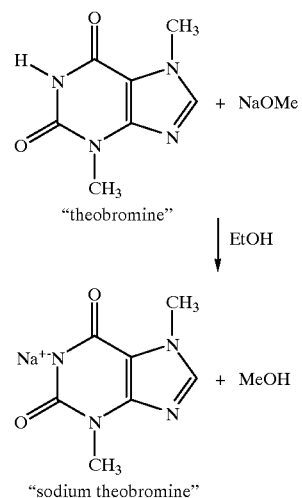

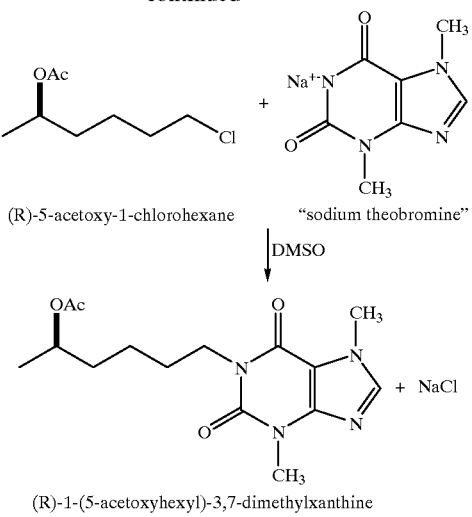

Finally, the ester precursor is reduced to obtain the secondary alcohol product in high yield and purity. The ester precursor is reacted with a mineral acid solution at a temperature ranging from +30 to +100° C. for a period of 0.25 to 6 hours. Examples of mineral acid solutions may be hydrochloric acid in water, methanol or ethanol. Methanol and ethanol are removed by distillation. Water is removed by azeotropic distillation. The intermediate salt is crystallized from a solvent. Representative solvents include, but are not limited to, acetone and methyl ethyl ketone. The salt is neutralized with a base and crystallized from a selected solvent, suitable neutralizing bases being, for example, potassium carbonate, potassium bicarbonate, sodium carbonate, and sodium bicarbonate. Recrystallization solvents include ethyl acetate, propyl acetate, isopropyl acetate, butyl acetate, and isobutyl acetate. Although other reagents are within the scope of the invention, preferred reagents may be methanol/concentrated hydrochloric acid (mineral acid solution), acetone (crystallization solvent), sodium bicarbonate (neutralizing base) and isobutyl acetate (recystallization solvent).

In a preferred embodiment of the inventive process, the chiral secondary alcohol precursor is a protected hydroxyalkyl group 5-(R)-acetoxy-1-chlorohexane ("chloroacetate"), which is subsequently coupled to a 3,7-dimethylxanthinyl moiety at the $N_1$ position to produce a preferred therapeutic agent: 1-(5-(R)-hydroxyhexyl)-3,7-dimethylxanthine. This product is produced with the starting materials ethyl (S)-(−)-lactate to form (R)-(+)-propylene oxide and propargyl alcohol.

Pharmaceutical Formulations

The pharmaceutical compositions of the invention generally contain a therapeutically effective amount of one or more compounds of the invention, or their pharmaceutically acceptable salts. Pharmaceutically acceptable salts readily will be apparent to the skilled clinician. Preferably, these one or more compounds, or their pharmaceutically acceptable salts, are admixed with a pharmaceutically acceptable excipient.

A suitable formulation will depend on the nature of the disorder to be treated, the nature of the medicament chosen, and the judgment of the attending physician. In general, the inventive compounds are formulated either for oral administration or injection, although other modes of administration such as transmucosal or transdermal routes may be employed. Suitable formulations for these compounds, including pharmaceutically acceptable excipients, can be found, for example, in REMINGTON'S PHARMACEUTICAL SCIENCES, chapters 83–92, pages 1519–1714 (Mack Publishing Company 1990) (Remington's), which is hereby incorporated by reference.

The inventive compounds and their pharmaceutically acceptable salts can be employed in a wide variety of pharmaceutical forms. The preparation of a pharmaceutically acceptable salt largely will be determined by the chemical nature of the compound itself, and can be prepared by conventional techniques readily available.

Thus, if a solid carrier is used then the preparation can be tableted, placed in a hard gelatin capsule in powder or pellet form or in the form of a troche or lozenge. The amount of solid carrier will vary widely but preferably will be from about 25 mg to about 1 gram.

Where the composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions or suspensions, for example, aqueous gums, celluloses, silicates or oils, may be considered and incorporated in a soft gelatin capsule shell.

When a liquid carrier is used, the preparation may be in the form of a syrup, emulsion, soft gelatin capsule, sterile injectable liquid such as an ampule or nonaqueous liquid suspension.

A syrup formulation will generally consist of a suspension or solution of the compound or salt thereof in a liquid carrier with a flavor or coloring agent. Examples of liquid carriers include ethanol, polyethylene glycol, coconut oil, glycerine and water.

Although other routes of administration are contemplated, the pharmaceutical compositions of the invention preferably are suitable for oral, intravenous, intraperitoneal, intramuscular, subcutaneous, parenteral, or topical delivery. Preferred administration is accomplished parenterally.

Parenteral administration can include intravenous ("i.v."), intramuscular ("i.m."), subcutaneous ("s.c."), intranasal, intrarectal, intravaginal or intraperitoneal ("i.p.") administration.

Additionally, the inventive compounds may be administered by, for example, intranasal or oral inhalation. Appropriate dosage forms for inhalation include an aerosol or a metered dose inhaler, as prepared by conventional techniques. Typical compounds for inhalation are in the form of a solution, suspension or emulsion that may be administered as a dry powder or in the form of an aerosol using a conventional propellant.

Appropriate dosage forms for each specific route of administration may be prepared by conventional techniques. A typical dosage form for parenteral administration is a solution or suspension of at least one inventive compound, or its pharmaceutically acceptable salt. The parenteral dosage form typically contains a parenterally acceptable sterile aqueous or non-aqueous carrier. The parenteral dosage form optionally contains a parenterally acceptable oil. Examples of such oils include polyethylene glycol, polyvinylpyrrolidone, lecithin, arachis oil, and sesame oil. Parenteral acceptability is known to the skilled clinician.

Formulation as a standard unit dose also is contemplated. Thus, the pharmaceutical compositions of the invention can be formulated, for example, for oral use in dosage unit form as a pill, a tablet, a caplet, or a capsule. These dosage units may each contain a therapeutically effective amount of one or more compounds of the invention. These dosage units also may contain sub-therapeutically effective amounts, where multiple units may be combined to achieve a therapeutically effective amount.

The amount of inventive compound in a unit dose will depend on many factors considered by the skilled clinician. Generally, however, dosage units prepared for oral use will contain from about 5 mg to about 5000 mg of compound of the invention. Preferred oral formulations contain from about 100 mg to about 2500 mg of compound, whereas other preferred formulations contain from about 500 mg to about 1500 mg. Such formulations conveniently can be administered one to six, and preferably, two or three times daily.

A typical parenteral unit dose can be from about 1 g to about 5 g and may be administered (i.v., i.p., i.m., or s.c.) over a course of 24 hours. A typical topical formulation contains from about 1% to about 4% inventive compound by weight.

The invention is illustrated by the following examples which should not be regarded as limiting the invention in any way.

EXAMPLE 1

This example shows the effect of LSF on the survival of mice exposed to 100% oxygen. Male BALB/c mice (20 grams) acclimatized to Denver altitude for 2 weeks. The mice were then placed in hyperoxia chambers at the Webb-Waring Institute, exposed to hyperoxic (100% $FiO_2$) conditions, and injected i.p. with 100 mg/kg LSF (200 $\mu$l/dose) in phosphate-buffered saline (PBS) or with PBS alone every 8 hours. FIG. 1 represents data obtained in this hyperoxia model. The mean survival time of mice exposed to 100% oxygen and injected i.p. with LSF was significantly improved over those mice exposed to similar amounts of oxygen and injected with only PBS. The data points for these study results are shown in the table below:

| Hour of Death (Post 100% $FiO_2$ exposure) for Each Animal | | |
|---|---|---|
| Animal No. | LSF | Control |
| 1 | 96 | 99 |
| 2 | 107 | 101.5 |
| 3 | 107 | 101.5 |
| 4 | 108 | 101.5 |
| 5 | 108.5 | 101.5 |
| 6 | 109 | 103 |
| 7 | 109 | 104 |
| 8 | 110.5 | 104 |
| 9 | 112 | 105 |
| 10 | 112.5 | 108.5 |
| 11 | 115.5 | 108.5 |
| 12 | 118 | 109 |
| 13 | 128 | 114 |
| 14 | 130 | 116 |
| 15 | 133.5 | 116.5 |
| 16 | 133.5 | 118 |
| 17 | 134 | 118.5 |
| 18 | 135 | 130 |
| 19 | 136 | 130 |
| 20 | 138 | 131.5 |

The mean difference in survival (mean of the control minus mean of LSF treated animals) is −7.975 (p<0.04), suggesting that mice treated with LSF survived about eight hours longer than placebo treated mice.

We claim:

1. A method for treating a condition resulting from hyperoxia comprising administering to an individual in need of such treatment a pharmaceutically effective amount of a compound of the formula

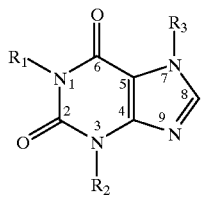

wherein:

$R_1$ is a substantially pure resolved R enantiomer ω-1, secondary alcohol-substituted ($C_{5-8}$) alkyl; and $R_2$ and $R_3$ are independently hydrogen atom or a ($C_{1-12}$) alkyl optionally containing one or two oxygen atoms in place of non-adjacent carbon atoms.

2. The method of claim 1 wherein the pharmaceutically effective amount is a prophylactically effective amount.

3. The method of claim 1 wherein the compound is 1-(R)-(5-hydroxyhexyl)-3,7-dimethylxanthine.

4. The method of claim 1 wherein the hyperoxia results from elevated inspired oxygen levels.

5. The method of claim 4 wherein the hyperoxia further results from elevated barometric pressure.

6. The method of claim 5 wherein the hyperoxia results from mechanical ventilation.

7. The method of claim 1 wherein the hyperoxia results from normal oxygen levels at ambient barometric pressure.

8. The method of claim 1 wherein the condition is selected from the group consisting of atelectasis, bronchopulmonary dysplasia, inflammation, tracheobronchitis, retinopathy of prematurity and seizures.

9. A method for treating conditions resulting from forced ventilation comprising administering to an individual in need of such treatment a pharmaceutically effective amount of a compound of the formula

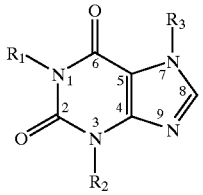

wherein:

$R_1$ is a substantially pure resolved R enantiomer ω-1, secondary alcohol-substituted ($C_{5-8}$) alkyl; and $R_2$ and $R_3$ are independently hydrogen atom or a ($C_{1-12}$) alkyl optionally containing one or two oxygen atoms in place of non-adjacent carbon atoms.

10. The method of claim 9 wherein the compound is 1-(R)-(5-hydroxyhexyl)-3,7-dimethylxanthine.

11. The method of claim 9 wherein the condition results from mechanical ventilation.

12. The method of claim 9 wherein the pharmaceutically effective amount is a prophylactically effective amount.

13. The method of claim 9 wherein the condition is inflammation resulting from pulmonary cellular damage.

* * * * *